Figure 1:
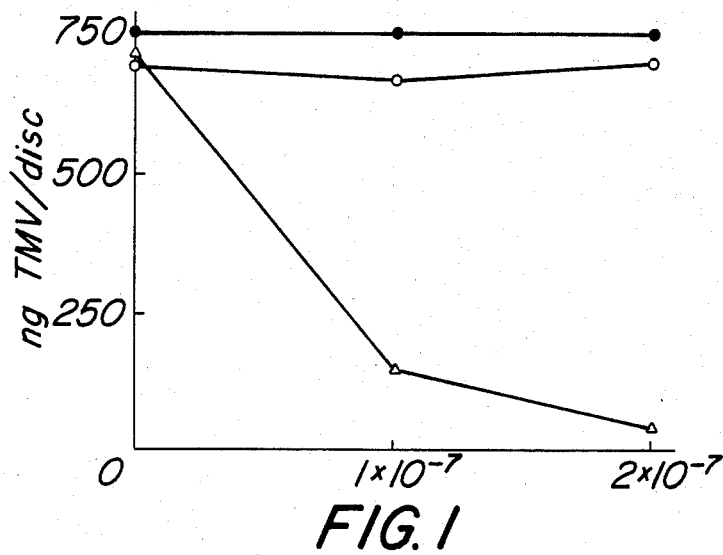

United States Patent [19]

Devash

[11] Patent Number: 4,654,326
[45] Date of Patent: Mar. 31, 1987

[54] INHIBITION OF PLANT VIRUSES WITH OLIGONUCLEOTIDES

[76] Inventor: Yair Devash, 2107 N. John Russell Cir., Elkins, Park, Pa. 19117

[21] Appl. No.: 630,058

[22] Filed: Jul. 12, 1984

[51] Int. Cl.$^4$ .............................................. A61K 31/70
[52] U.S. Cl. ........................................ 514/47; 514/48; 514/49; 536/27; 536/28; 536/29
[58] Field of Search ................... 424/180, 181; 536/27, 536/28, 29; 514/47, 44, 48

[56] References Cited

PUBLICATIONS

Devash et al., Multiplication of Tobacco Mosaic Virus in Tobacco Leaf Discs is Inhibited by (2'-5') Oligoadenylate, Chem Abstracts 97:36235x (1982).
Reichman et al., Human Leukocyte Interferon and the Antiviral Factor (AVF) from . . . Plants Stimulate Plant . . . Nucleotides with Antiviral Activity, Chem Abstracts 99:156589d (1983).
Eppstein et al., Analogs of PPP (A2'P)nA. Correlation of Structure . . . with Stability and Biological Activity, Chem Abstracts 98:32781v (1983).
Devash et al., 5'-Dephosphorylated 2',5'-Adenylate Trimer . . . Inhibition of Tobacco Mosaic Virus in . . . Intact Tobacco Plants, Chem Abstracts 100:188949b (1984).

*Primary Examiner*—Johnnie R. Brown
*Attorney, Agent, or Firm*—Caesar, Rivise, Bernstein, Cohen & Pokotilow, Ltd.

[57] ABSTRACT

Viral diseases in plant parts, such as leaves are inhibited by applying to the plants an effective amount of an agent comprising 2', 5'-oligonucleotide, such as 2, 5-A, linked in 2', 5'-phosphodiester bond. The agent is provided in a vehicle such as a liquid or a powder, and is present in the vehicle in an effective amount at a concentration less than $1 \times 10^{-8}$ M.

8 Claims, 2 Drawing Figures

INHIBITION OF PLANT VIRUSES WITH OLIGONUCLEOTIDES

BACKGROUND OF THE INVENTION

This invention relates to the use of a very wide class of 2',5'-oligoadenylates and their analogs (2',5'-oligonucleotides) linked in a 2',5'-phosphodiester bond to inhibit viral diseases in plants, plant tissues, leaves and other parts.

In Devash et al, Science 216, 1415–1416 (1982), the disclosure of which is completely incorporated herein by reference, it was shown that 2',5'-oligoadenylates, a family of compounds which are induced in interferon treated animal cells, and their analogs (2',5'-oligonucleotides) is induced in interferon treated animal cells, protects plant tissue from infection by the tobacco mosaic virus (TMV). The basis 2',5'-oligoadenylate is referred to as 2,5-A or 2',5'A. This inhibition of virus multiplication was obtained in concentrations comparable to those affecting protein synthesis and antiviral activities in animal cells. After one hour treatment with (2',5') oligoadenylates, the multiplicity of tobacco mosaic virus was reduced by 80 to 90% with concentrations of 100 to 200 nM 2,5-A being sufficient to achieve near-total inhibition. However, it was noted that the 2,5A must be applied to the TMV infected tissue early in infection to obtain a maximum antiviral affect.

By virtue of the present invention the present inventor who is the lead author in the 1982 Devash et al. publication, has now determined there is a very wide class of 2',5'-oligoadenylates and 2',5'-oligonucleotide analogs linked in a 2',5'-phosphodiester bond which are effective in extremely low concentration to inhibit replication of tobacco mosaic virus (TMV) and a broad spectrum of viral diseases in plants.

It is known that protection is conferred to virus-infected mammalian cells by the formation of interferon which induces the synthesis of at lease two enzymes. One of these enzymes is the 2',5'-adenylate synthetase which in the presence of certain double-stranded RNAs converts adenosine triphosphate (ATP) to a series of unique 2',5'-oligoadenylates.

In addition to the synthesis of the 5'-triphosphate 2',5'-linked oligoadenylates, there have been reports concerning the intracellular accumulation of the 5'-dephosphorylated 2',5'-adenylate molecules (referred to here as 2',5'-adenylate cores) in mouse L-cells following treatment with interferon. It was concluded that because the amount of cores seemed to be independent of the concentration of the 2',5'-oligoadenylate 5'-triphosphate molecule, 2',5'-oligoadenylate cores may play a separate role in the inhibition of DNA-synthesis and cellular reactions.

Because of the rapid hydrolysis of the naturally occurring 2',5'-oligoadenylate molecule in cells, there have been reports on the enzymatic and chemical synthesis of the 2',5'-oligoadenylate, 5'-triphosphate analogs and their corresponding cores in attempts to increase the metabolic stability and retain inhibition of protein syntheses. In addition, it has been reported that the 5'-diphosphate of 3',5'-adenylate molecule activated the 2',5'-A$_n$-dependent endonuclease to hydrolyze mouse L-cell rRNA. Also, the 2',5'-cordycepin tetramer 5'-triphosphate analog complexes with and activated the 2',5'-A$_n$-dependent endonuclease to hydrolyze vesicular stomatitis virus mRNA and inhibit protein synthesis.

Because of the natural occurrence of the 2',5'-oligoadenylate core in mammalian cells, various laboratories have studied the effect of core compounds on cellular processes in animal cells, tumor growth in whole animals, and inhibition of virus replication in plants. For example, it has been demonstrated that the 2',5'-oligoadenylate cores and 2',5'-cordycepin trimer core inhibit transformation of Epstein-Barr virus-infected lymphocytes by inhibiting the synthesis of the Epstein-Barr virus-induced nuclear antigen, augment natural killer cell activity, inhibit TMV replication in tobacco plants, and inhibit chondrosarcoma growth in animals.

It has been demonstrated that the 2',5'-oligoadenylate core analogs do not exert their action by 5'-rephosphorylation followed by activation of the 2',5'-A$_n$-dependent endonuclease. There have been suggestions that cores may act by pathways independent of interferon.

It has been further reported that 2',5'-cores act as prodrugs due to degradation by esterases. However, this does not appear to be the case in all mammalian cell systems. For example, it has been demonstrated that tritium-labeled 2',5'-cordycepin trimer core is taken up intact by human lymphocytes.

Recently, it has been reported that human recombinant leukocyte interferon inhibited TMV replication in tobacco leaf discs. Furthermore, the antiviral factor isolated from TMV-infected leaves of *Nicotiana glutinosa* and human leukocyte interferon induced double-standed RNA-dependent synthesis of oligoadenylates from ATP in plants, producing oligonucleotides with antiviral activity.

In the present invention a very wide class of oligodenylates and oligonucleotides analogs linked in a 2',5'-phosphodiester bond with a chain length of dimer up to ten nucleosides long, with or without external phosphates inhibit TMV replication in TMV-infected tobacco leaf discs, TMV-infected protoplasts, and in whole plants.

The adenosine molecule has the following structure:

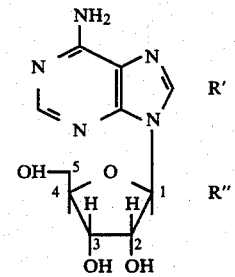

R' above is known as the aglycone moiety. R" above is known as the ribosyl or the ribosyl sugar moiety. It is well known that either the aglycone or the ribosyl can be modified in various ways. For instance, the 6-amino group on the aglycone (adenosine) can be substituted by a hydroxyl group to form inosine. Alternatively the 7 position nitrogen atom of adenosine can be substituted by a carbon atom to form tubercidin.

In the ribosyl, the hydroxyl group in the 3' position can be substituted by hydrogen to form cordycepin, or the hydrogen and the hydroxyl groups can change positions on the 2' carbon to form ara-A or a hydrogen and hydroxyl groups can change position on the 3' to form xylo-A.

Moreover, the inhibition effects observed in the present invention on plant viruses is applicable to all the foregoing variations in 2,5-A as well as other modifications of the basic adenosine structure regardless of the modifications on either the aglycone or the rybosyl or both so long as the oligoadenylate or the oligonucleotide analogs are linked in a 2',5'-phosphodiester bond.

The present invention also encompasses the so-called core compounds as well as the unique series of oligoadenylate 5'-triphosphate PPPA(2'p5'A)$_n$ which are commonly known as 2,5-A. The core differs from 2,5-A itself or 2,5-A related compounds, since the core lacks the 5'-terminal triphosphates. The present invention also encompasses (1) the existence of any external phosphate (i.e., mono, di, tri and tetra phosphates present in either the 5',2' or 3' positions) (2) variations in the aglycone or ribosyl as discussed hereinabove. The present invention further includes the dimer, trimer, tetramer and up to 2',5'-oligonucleotides with a chain length of up to ten nucleosides, (r=10). The trimer is illustrated below:

tion which induces the synthesis of 2',5'-linked oligoadenylates. In the plant cell, an antiviral factor has been isolated from *N. glutinosa* (N.-gene carrying plants in which the infection in the intact plant is localized) leaves infected with TMV. A substance inhibiting virus replication has also been reported to be released from TMV-infected protoplasts of the *N. glutinosa* cultivar. These inhibitors may be the "protectors" of plants from virus infection. It has been demonstrated that some human interferon preparations inhibited TMV replication in tobacco leaf discs. Application of the 2',5'-adenylate trimer core to TMV-infected tobacco leaf discs also inhibited TMV replication. TMV, antiviral factor, or interferon induces an enzyme capable of converting ATP to putative oligoadenylates with the ability to inhibit TMV replication. These oligoadenylates inhibit protein synthesis when added to either lysates from rabbit reticulocytes or wheat germ extracts via a mechanism different from the 2',5'-A$_n$-dependent endonuclease activation. Previous reports indicate that 2',5'- adenylate trimer core and 2',5'-cordycepin trimer core protect plant cells against viral infection. The present invention demonstrates the potency of 2',5'-adenylate

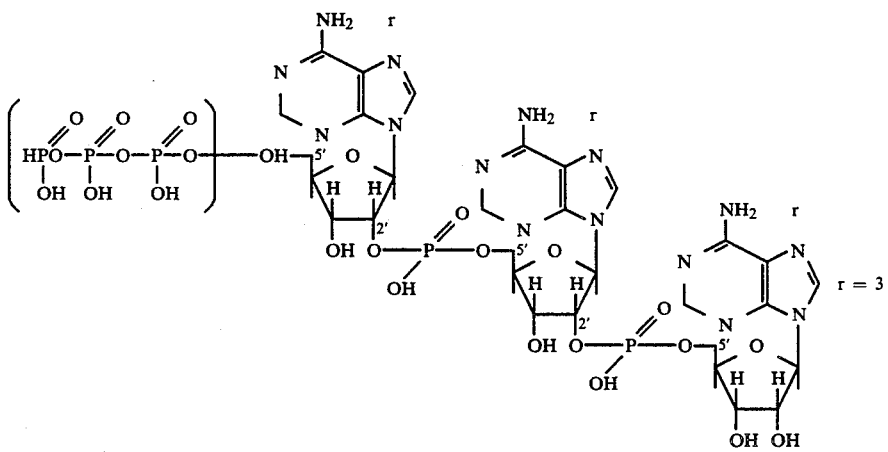

In view of the foregoing it is very clear that the present invention applies to any oligomer of 2',5' of any size where r=2 to r=10.

Moreover, the present invention includes any modifications on the internal and external phosphodiester bonds, such as modifications on the bridged oxygens as well as any modifications on the non-bridged oxygen (double bond phosphorous). The present invention is also applicable to any change on the phosphonyl group.

Accordingly, by way of example only and without limitation it follows that there are many compounds covered by this invention, so long as there is the 2',5'-phophodiester bond as discussed herein above. Exemplorary of compounds falling within the scope of the present invention are 2',5'-adenylate dimer or trimer cores, 2',5'-cordycepin trimer cores, 2',5'-inosinate dimer trimer cores, adenylyl-(2' 5')-adenylyl-(2' 5')-9-β-D-arabinofuranosyladenine; adenylyl-(2' 5')-adenylyl-(2' 5)-tubercidin.

MATERIALS AND METHODS AND RESULTS

Viral diseases occurring in the animal kingdom and in the plant kingdom present serious problems. Therefore, it is important to understand how the animal and plant cell are protected from virus infection. In the animal cell, interferon is synthesized in response to virus infectrimer core and its 2',5'- analogs as well as all other compounds as suggested above and those which will occur to one skilled in the art. Specifically, the present invention demonstrates the ability of the aforesaid compounds to inhibit TMV and other viral disease replication in protoplasts, TMV-infected leaf discs, and in the whole plant. In all experiments, the 2',5'-trimer cores were potent inhibitors of TMV replication at nanomolar concentrations. It is not yet clear whether passive equilibrium, uptake, binding, or a combination of uptake and binding is the mechanism by which the inhibition of TMV replication occurs.

Chemical. The 2',5'-trimer cores of adenosine, inosine, cordycepin, A-A-Tu and A-A-ara-A were synthesized in a manner that is well known to those skilled in the art. Cordycepin 5'-monophosphate and tubercidin 5'-monophosphate were synthesized and isolated. Tubercidin was obtained from Upjohn Company. 2',5'-cordycepin trimer core was labeled with tritium by Abersham Corp. and purified to constant specific activity of 140 μCi/μmole by paper chromatography and HPLC. 2',5'-oligoadenylate core was enzymatically synthesized with a specific activity of 11.5 Ci/m mole. All other chemicals were of the purest form commercially available.

Plant material treatment and measurement of infectivity. Partially purified AVF was prepared. The growth of *N. glutinosa*, *N. tabacum* Var. "Samsun", *N. tabacum* cv. Samsun NN, and preparation and inoculation of protoplasts were as described. To evaluate the effect of 2',5'-cores, nucleotides and nucleosides on TMV replication, various concentrations were added to 10 ml of protoplast suspension ($1 \times 10^5$ cells/ml) at various times after inoculation with TMV. Protoplasts were incubated at 25° C. under continuous illumination of about 1500 Lx. At various times protoplasts were collected by centrifugation and homogenized. The homogenate was inoculated onto 12 half-leaves of *N. glutinosa* plants and compared to a standard solution of purified TMV on the opposite half-leaves. Lesion counts were adjusted to $10^6$ live protoplasts and calibrated. Control protoplasts (no Nucleotides added) were assayed simultaneously. The assays for antiviral activity on TMV-infected tobacco leaf discs were done by enzyme-linked immunosorbent assay. The ability of the 2',5'-cores, nucleosides, and nucleotides to inhibit TMV replication in the intact plant was determined by infectivity tests as follows. Solutions containing 5 μg/ml TMV, 0.1 g carborundum (100 Tyler mesh), and 2',5'-cores, nucleosides, or nucleotides were applied onto 12 half-leaves of *N. glutinosa*. The remaining half-leaves were controls (inoculated with a solution containing no nucleotides). The infection was allowed to proceed 48 hours under continuous illumination.

Association of 2',5'-[$^3$H] cordycepin trimer core with plant leaves. Infecting solution containing TMV, carborundum and 2',5'-[$^3$H] cordycepin trimer core ($2 \times 10^{-6}$ M, $6.25 \times 10^5$ dpm/ml) was used to infect 20 half-leaves of *n. glutinosa*. At 0, 3, 6, and 24 hours after infection, leaves were removed and $1 \times cm^2$ pieces were out. The leaf pieces were homogenized in 1 ml of 0.01 M NaH$_2$PO$_4$ buffer, pH 7.6, and the radioactivity was determined.

Assays for the metabolic stability of 2',5'-adenylate trimer core. Erhlich ascites tumore (EAT) cell and Raji cell lysates were prepared. TMV-infected or non-infected *N. glutinosa* leaf extracts were prepared by homogenizing leaves (1:1, w/v) in 0.01 M NaH$_2$PO$_4$, pH 7.6, followed by centrifugation(10,000 × g, 4° C., 10 min); the supernatants were used as plant cell lysates. Animal and plant lysates were used as the source of 2',5'-phosphodiesterase activity. Incubation mixtures (10 μl) contained 2 or 4 μl lysates, 2.5 μl buffer (80 nM Tris-HCl, pH 8.0, 80 nM Mg (OAc)$_2$, 4 nM DTT) and 2',5'-[$^3$H]adenylate trimer core (20,000 dpm). Incubations were at 30° C., 2 hours. Incubation tubes were centrifuges (1,000 × g, 4° C., 10 min.) and the supernatants were applied to thin layer chromatograms (Brinkman PEI-cellulose, solvent: 0.1 N LiCl). UV markers migrated on the thin layer chromatography as follows: Adenosine (Rf=0.55), AMP (Rf=0.11), and 2',5'-adeylate trimer core (Rf=0.05).

RESULTS

Effect of 2',5'-addenylate trimer core and 2',5'- analogs on TMV replication in tobacco proproplasts. It was previously demonstrated that 2',5'-adenylate trimer core and its 2',5'-cordycepin analog were potent inhibitors of TMV-replication in TMV-infected leaf discs of *N. tabacum*. However, to assess more accurately the effect of the trimer cores on the inhibition of TMV replication, protoplasts were prepared. At $1 \times 10^{-8}$ M, 2',5'-adenylate trimer core in protoplasts medium inhibited TMV replication 53% after 72 hours (Table 1). The inhibition of virus replication by the 2',5'-adenylate trimer core was dose dependent. 2',5'-adenylate trimer core and 2',5'-cordycepin trimer core inhibited TMV replication 93% and 96%, respectively, at $1 \times 10^{-7}$ M. 3',5'-adenylate trimer core was of similar potency to AMP. The 2',5'-inosinate trimer core caused about 50% inhibition of TMV replication at $1 \times 10^{-7}$ M. Adenosine, AMP, cordycepin, 3' dAMP, and inosine (possible degradation products) were less inhibitory. A maximum antiviral effect was obtained when the 2',5'-cores were added earlier than 5 hours after inoculation with TMV (Table 2). The antiviral effect was decreased when cores were added 5 and 12 hours after infection (Table 2). Adenosine and AMP showed no inhibition of TMV replication in tobacco leaf discs up to $2 \times 10^{-7}$ M when compared to total inhibition of TMV replication by the 2',5'-adenylate trimer core (FIG. 1).

Figure 2:
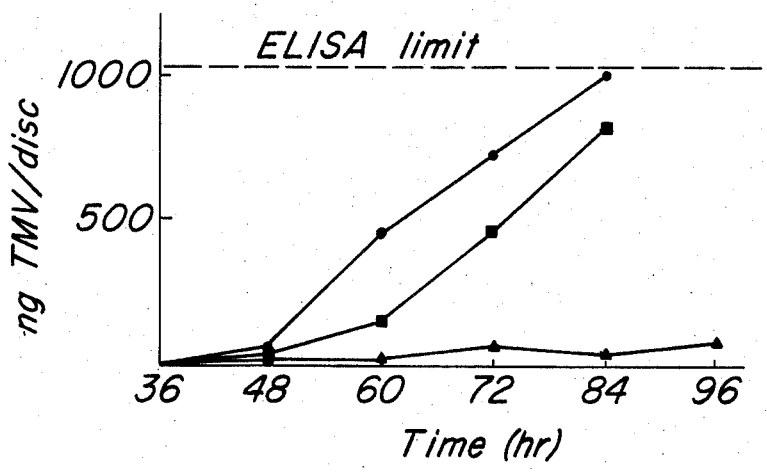

Inhibition of TMV replication by 2',5'-trimer cores with increasing time. Also tested were the kinetics of the inhibition of TMV-replication by the 2',5'-adenylate trimer core and the 2',5'-cordycepin trimer core in infected leaf discs. Tobacco leaf discs inoculated with TMV were treated for an additional hour with 200 nM 2',5'-adenylate trimer core or 200 nM 2',5'-cordycepin trimer core. The discs were then washed and the infection was allowed to proceed. Virus replication was totally inhibited for 60 hours by 2',5'-adenylate trimer core and the inhibitory effect gradually diminished from 60 to 96 hours. However, TMV inhibition by the 2',5'-cordycepin trimer core was noted for 96 hours (FIG. 2). The extended inhibitory activity of the 2',5'-cordycepin trimer core compared to the naturally occurring adenylate core may be due to increased stability of the analog, and effect of increased uptake, or a different inhibitory mechanism.

Effect of 2',5'-adenylate trimer core and its analogs on TMV replication in intact plants. The 2',5'-adenylate trimer core, 2',5'-cordycepin trimer core, 2',5'-inosinate trimer core, 2',5'-A-A-ara-A, and 2',5'-A-A-Tu, were potent inhibitors of TMV replication when applied to leaves of *N. glutinosa* at $1 \times 10^{-6}$ M in the TMV-infecting solution. The cores inhibited the formation of local lesions following TMV infection by 89–99% (Table 3). The nucleosides and nucleotides were not antivirally active or exhibited negligible activity at $1 \times 10^{-6}$ M.. 2',5'-adenylate trimer core, 2',5'-cordycepin trimer core, and 2',5'-inosinate trimer core inhibited TMV replication in a dose-dependent manner. The 2',5'-inosinate trimer core was not as good (68% inhibition at $1 \times 10^{-6}$ M) as 2',5'-adenylate trimer core and 2',5'-cordycepin trimer core (91% and 93% inhibition at $1 \times 10^{-6}$ M, respectively)(Table 4). Non-infected plants were treated with $1 \times 10^{-6}$ M 2',5'adenylate trimer core, 2',5'-cordycepin trimer core, 2',5'-A-A-ara-A, and 2',5'-A-A-Tu (data not shown). No toxicity (chlorosis or necrosis) was observed during the two week period tested.

TABLE 1

The Inhibition of TMV Replication in Tobacco Protoplasts by 2',5'-Adenylate Trimer Core and Analogs[a]

| Nucleotide Added | Concentration (M) | Inhibitions[b] After 24 hr (%) | After 48 hr (%) | After 72 hr (%) |
|---|---|---|---|---|
| No addition | — | 0 | 0 | 0 |
| 2',5'-Adenylate trimer core | $1 \times 10^{-8}$ | 48($P < 0.01$) | 41($P < 0.01$) | 53.0($P < 0.01$) |
|  | $1 \times 10^{-7}$ | 92($P < 0.01$) | 93($P < 0.01$) | 92($P < 0.01$) |
| 3',5'-Adenylate trimer core | $1 \times 10^{-7}$ | 27($P < 0.01$) | 38($P < 0.01$) | NO |
| Adenosine | $1 \times 10^{-7}$ | 14($P < 0.01$) | 0 | NO |
| AMP | $1 \times 10^{-7}$ | 22($P < 0.01$) | 33($P < 0.01$) | NO |
| 2',5'-Cordycepin trimer core | $1 \times 10^{-7}$ | 95($P < 0.01$) | 96($P < 0.01$) | NO |
| Cordycepin | $1 \times 10^{-7}$ | NO[c] | 21($P < 0.01$) | 32($P < 0.01$) |
| 3' CAMP | $1 \times 10^{-7}$ | NO | 41($P < 0.01$) | 45($P < 0.01$) |
| 2',5'-Inosinate trimer core | $1 \times 10^{-7}$ | 53($P < 0.01$) | 54($P < 0.01$) | NO |
| Inosine | $1 \times 10^{-7}$ | NO | 22($P < 0.01$) | 25($P < 0.01$) |

[a] 2',5'-or 3',5'-trimer cores, nucleosides and nucleotides were added to the TMV-infected protoplasts within 3 hours of infection.
[b] Average of four experiments. Inhibition of TMV replication observed by the 2',5'-cores, nucleosides and nucleotides was calculated as the percent of local leasions produced in *N. glutinosa* treated by homogenates of protoplasts compared to non-treated protoplasts.
[c] Not determined.

TABLE 2

Inhibition of TMV Replication In Tobacco Protoplasts Treated with 2',5'-Adenylate Trimer Core and Analogs at Various Times After Infection

| Compound Added[a] | Time of addition (hr after inoculation) Inhibition[b] After 0 hr (%) | After 5 hr (%) | After 12 hr (%) |
|---|---|---|---|
| No addition | 0 | 0 | 0 |
| 2',5'-Adenylate trimer core | 78($P < 0.01$) | 59($P < 0.01$) | 44($P < 0.01$) |
| 3',5'-Adenylate trimer core | 31($P < 0.01$) | 24($P < 0.01$) | 23($P < 0.01$) |
| 2',5'-Cordycepin trimer core | 79($P < 0.01$) | 66($P < 0.01$) | 53($P < 0.01$) |
| 2',5'-Inosinate trimer core | 60($P < 0.01$) | 50($P < 0.01$) | 37($P < 0.01$) |

[a] Final concentration of 2',5'-oligonucleotide trimer cores in protoplast medium was $5 \times 10^{-8}$ M.
[b] Inhibition of TMV replication was determined 48 hours after infection and calculated as in Table 1, footnote b.

TABLE 3

Effect of 2',5'-Adenylate Trimer Core, 2',5'-Trimer Core Analogs, Nucleosides and Nucleotides on TMV Replication in *N. glutinosa* Leaves

| Addition[a] | Inhibition[b] (%) |
|---|---|
| No Addition | 0 |
| 2',5'-Adenylate trimer core | 93($P < 0.01$) |
| 2',5'-Cordycepin trimer core | 99($P < 0.01$) |
| 2',5'-Inosinate trimer core | 92($P < 0.01$) |
| 2',5'-A-A-ara-A | 94($P < 0.01$) |
| 2',5'-A-A-Tu | 95($P < 0.01$) |
| AMP | 10 |
| Cordycepin monophosphate | 0 |
| IMP | 10($P < 0.05$) |
| Ara-AMP | 0 |
| TuMP | 0 |
| Adenosine | 0 |
| Cordycepin | 0 |
| Inosine | 0 |
| Ara-a | 0 |
| Tubercidin | 0 |
| MOCK AVF[c] | 0 |
| AVF | 95($P < 0.01$) |

[a] Additions were as described in Materials and Methods. Add additions were at $1 \times 10^{-6}$ M in the infecting solution.
[b] Inhibition of TMV replication was determined 48 hours after infection and calculated as in Table 1, footnote b.
[c] Partially purified AVF (50 ng protein/ml) prepared as described in Materials and Methods was added to TMV-containing solution at a dilution of $1 \times 10^{-3}$.

TABLE 4

Effect of various Concentrations of 2',5'-Adenylate Trimer Core, 2',5'-Cordycepin Trimer Core, and 2',5'-Inosinate Trimer Core on TMV Replication in *N. glutinosa* Leaves[d]

| Oligonucleotide Added | Concentration (M) | Inhibition (%) |
|---|---|---|
| No addition | — | 0 |
| 2',5'-Adenylate trimer core | $1 \times 10^{-6}$ | 91($P < 0.01$) |
|  | $1 \times 10^{-7}$ | 80($P < 0.01$) |
|  | $1 \times 10^{-8}$ | 75($P < 0.01$) |
| 2',5'-Cordycepin trimer core | $1 \times 10^{-6}$ | 93($P < 0.01$) |
|  | $1 \times 10^{-7}$ | 84($P < 0.01$) |
|  | $1 \times 10^{-8}$ | 76($P < 0.01$) |
| 2',5'-Inosinate trimer core | $1 \times 10^{-6}$ | 68($P < 0.01$) |
|  | $1 \times 10^{-7}$ | 50($P < 0.01$) |
|  | $1 \times 10^{-8}$ | 36($P < 0.01$) |

[d] Leaves were as described in Materials and Methods.

Association of 2',5'-[$^3$H] Corcycepin trimer core with plant leaves. In order to determine the amount of 2',5'-trimer core associated with the plant leaves ($2 \times 10^{-6}$ M $6.25 \times 10^5$ dpm/ml0), 2',5'-[$^3$H] cordycepin timer core (in infecting solution was applied to half-leaves as described in Materials and Methods. Only 0.125% of the 2',5'-[$^3$H] cordycepin trimer core present in 1 ml of the infecting solution was associated with the leaves (Table 5). Therefore, when 2',5'-cordycepin trimer core in the infecting solution is at a concentration of $2 \times 10^{-6}$ M, only $2 \times 10^{-12}$ moles are associated with each $1 \times$ cm$^2$ of leaf. Therefore, when $1 \times 10^{-8}$ M is used (Table 5) only $1 \times 10^{-14}$ moles of active ingredient are necessary to be associated with each square centimeter of plant leaf. See Tables 4 and 5. About 50% of the $2 \times 10^{-12}$ moles of 2',5'-[$^3$H] cordycepin trimer core remained associated with the leaves after extensive washing. No triarium was detected in the untreated half-leaves (Table 5), indicating little or no systematic spread of the nucleotides.

Metalbolic stability of 2',5'-adenylate trimer core in plant extracts. 2',5'-adenylate trimer core has been shown to affect mammalian cells at a micromolar concentration (15–27, 30, 31), whereas it inhibits TMV replication at nonmolar concentration (28–29) (Tables 1–4, FIGS. 1, 2). Hence, we compared the metabolic stability of 2',5'-adenylate trimer core in lysates of two mammalian cell lines and plant leaves. The assays were done as described in Materials and Methods. 2',5'-[$^3$H] adenylate trimer core was hydrolysed to adenosine and AMP by the 2',5'-phosphodiesterase present in EAT or Raji cells (Table 6). However, little hydrolysis of 2',5'-[$^3$H] adenylate trimer core occurred in TMV-infected and non-infected plant leaf extracts (Table 6).

TABLE 5

Association of 2',5'-[$^3$H]Cordycepin Trimer Core with N. glutinosa Leaves[a]

| Time after Infection hr | $^3$H/l m cm$^2$ Treated leaf[b] | | $^3$H/l m cm$^2$ Untreated leaf[b] | |
|---|---|---|---|---|
| | Unwashed (dpm)[d] | Washed[c] (dpm) | Unwashed (dpm) | Washed[c] (dpm) |
| 0 | 720 | 457 | 14 | 15 |
| 3 | 782 | 502 | 21 | 19 |
| 6 | 725 | 385 | 23 | 18 |
| 24 | 705 | 427 | 17 | 19 |

[a]Assays were done as described in Materials and Methods.
[b]Average of five 1 × cm$^2$ leaf pieces.
[c]1 × cm$^2$ leaf pieces were washed five times in three liters of 0.01 M NaH$_2$PO$_4$.
[d]625 dpm m 2 × 10$^{-12}$ moles of 2',5'-[$^3$H]cordycepin trimer core.

TABLE 6

Hydrolysis of 2',5'-[$^3$H]Adenylate Trimer Core by Ehrlich Ascites Tumor and Rail Cell Lysates and TMV-Infected and Non-Infected N. glutinosa Leaf lysates[a]

| | Products | | |
|---|---|---|---|
| Hydrolysis Conditions | [$^3$H]adenosine (%)[b] | [$^3$H]AMP (%) | 2',5'-[$^3$H]— adenylate trimer core (%) |
| No additions | 3 | 4 | 93 |
| No additions, 30° C., 2 hr | 5 | 3 | 92 |
| SVPD[c] | 24 | 75 | 1 |
| EAT cell lysates | | | |
| (2 μl) | 11 | 64 | 25 |
| (4 μl) | 17 | 72 | 11 |
| Raji cell lysates | | | |
| (2 μl) | 21 | 74 | 5 |
| (4 μl) | 21 | 77 | 2 |
| Non-infected N. glutinosa | | | |
| (2 μl) | 7 | 8 | 85 |
| (4 μl) | 10 | 5 | 85 |
| TMV-infected N. glutinosa | | | |
| (2 μl) | 5 | 7 | 88 |
| (4 μl) | 5 | 5 | 90 |

[a]Assays were done as described in Materials and Methods.
[b]Percent hydrolysis (average of three experiments) was calculated as $\frac{\text{dpm of product}}{\text{total dpm}} \times 100$.
[c]Snake venom phosphodiesterase (SVPD) hydrolyses.

FURTHER OBSERVATIONS

A structure-activity-metabolic stability-toxicity relationsion of the 2',5'-adenylate trimer core in TMV-INFECTED N. glutinosa was determined. Replacement of the 6-amino group of the adenylate residues in 2',5'-adenylate trimer core with a 6-hydroxyl group (i.e., inosinate trimer core) resulted in a derivative that inhibited TMV replication. When the 2'-terminal adenylate was replaced by either ara-A or tubercidin (i.e., A-A-ara-A or A-A-Tu), the resulting trimer cores also inhibited TMV replication. When the 3'-hydroxyl of 2',5'-adenylate trimer core was replaced by a hydrogen atom (i.e., the cordycepin trimer core), TMV replication was inhibited better than that observed with the naturally occurring 2',5'-adenylate trimer core. None of these oligoadenylate analogs were toxic to N. glutinosa. Structural modification of the ribose on the 2'-terminal nucleotide in the 2',5'-oligoadenylate molecule results in analogs that are considerably more stable to hydrolysis by the 2',5'-phosphodiesterase in the mammalian system; however, 2',5'-phosphodiesterase activity was not detected in N. glutinosa. The fact that there is no increase in hydrolysis of 2',5'-[$^3$H]adenylate trimer core in TMV-infected or uninfected N. glutinosa when the amount of cell-free extract was doubled suggests that there is no 2',5'-phosphodiesterase activity as determined under these assay conditions (Table VI). In contrast to the leaf discs and intact plants, where the degradation products of 2',5'-adenylate trimer core and analogs did not inhibit TMV replication (Table III and FIG. 1), in protoplasts a different inhibitory mechananism appears to exist because 3',5'-adenylate trimer core, AMP, and adenosine showed some inhibition of TMV replication (Tables I and II). The increased inhibition of TMV replication by the 2',5'-cordycepin trimer core may be attributed to increased stability to other 2',5'-adenylate degradative enzymes in plants or the inhibition of RNA, DNA, or protein synthesis. The concentrations of 2',5'-adenylate trimer core and trimer analogs required for the inhibition of TMV replication in plants are 1000-fold lower than the concentrations required for the inhibition of transformation of Epstein-Barr virus-infected blyphocytes, the inhibition of tumor growth, the antimitogenic effect, and the antiproliferative effects reported in mammalian systems. As will be explained $10^{-14}$ moles (10 fentomoles) are sufficient to inhibit TMV to about 75%. The 1000-fold difference could be explained by the metabolic stability of 2',5'-adenylate trimer core in plants due to lack of 2',5'-phosphodiesterase activity (Table VI). These observations are in contrast to reports that 2',5'-cores act as prodrugs in some mammalian systems due to degradation by esterases. This does not appear to be the case in all mammalian cell systems. For example, it has been reported that 2',5'-cordycepin core trimer is taken up intact by human lymphocytes.

It was previously reported the induction of a plant oligoadenylate synthetase which converted ATP into oligoadenylates when immobilized on poly(rI)-poly(rC). The plant oligonucleotides inhibited TMV replication. More recently, it has been shown that these same oligoadenylates, following purification by high pressure liquid chromatography, inhibit protein synthesis in lysates from rabbit reticulocytes; however no 2',5'A$_n$-dependent endonuclease or 2',5'-phosphodiesterase activity was detected in uninfected or TMV-infected plants. Similarly, it has been reported that the 5'-triphosphate of the 2',5'-oligoadenylate or its binding proteins were not present in tobacco plants.

The present invention demonstrates by way of nonlimiting example that the inhibition of TMV replication in intact *N. glutinosa* occurs with the 2′,5′-adenylate trimer core, 2′,5′-inosinate trimer core, 2′,5′-cordycepin trimer core, 2′,5′-A-A-ara-A. Earlier studies also showed that the 5′-triphosphate of the 2′,5′-adenylate trimer molecule, when applied to TMV-infected leaf discs, also inhibited TMV replication. There is the possibility that 2′,5′-trimer cores inhibit TMV replication via the activation of plant discharging factor to discharge aminoacylated TMV RNA, which inhibits viral protein synthesis. Further studies on the effect of 2′,5′-adenylate molecule on plant protein, RNA and DNA synthesis, activation of discharging factor, viral coat protein synthesis, TMV RNA synthesis, and virus assembly are in progress. Abrasion of the plant leaf epidermis with a TMV/carborundum solution containing very dilute solutions of the 2′,5′-adenylate core or 2′,5′-analogs results in inhibition of TMV replication without any toxicity to the plants. This novel approach to the inhibition of viral replication may have a great potential in the control of plant virus infections.

COMPOSITIONS AND USE

In Devash et al., *Science* 216, 1415–1416 (1982) and Reichman et al. *Virology* 128, 240–244 (1983), it had been determined that 2-5A requires a calcium phosphate coprecipitation technique to penetrate into plant cells. However, in the present invention it has been determined that no such coprecipation technique is needed. Instead, the active ingredient, such as 2-5A or 2-5A core, is simply dissolved in water and such solution can be applied either to the roots or the leaves of the plants in various ways by those skilled in the art. Such solution can be applied to the roots of the plant through irrigation or spraying from above by land or air vehicles or by pressure spraying. Spraying can be enhanced by the inclusion in the composition of fine particules of carborundum which as previously discussed have an abrasive effect on the leaves of the plant to facilitate entry of the active ingredient into the plant system. A preferred 2-5A core, water and carborundum solution is applied to the plants once each week at a rate of as low as one milligram active ingredient per acre, although frequency of application, the concentration of active ingredient used can be varied in accordance with determinations readily made by those skilled in the art.

As noted in Tables IV and V, the effective concentrations of active ingredient are those as low as $1 \times 10^{-14}$ moles where 75% inhibition was observed.

In a preferred composition, an aqueous solution using water having a pH of 7.0 (n buffered to pH 7.0) the 2,5-A was present in a concentration of $1 \times 10^{-8}$ M and was applied weekly to growing tobacco plants (*N. tabacum*) at a rate of 1 milligram per acre active ingredient (2,5-A). Carborundum was present in an amount 70.1 g/ml.

Typical plant viral diseases inhibited by the methods of the present invention include mosaic viruses associated with cucumbers, wheat, tobacco, squash, lettuce, cotton, sugar beet, various flowers. Other plant viral diseases include viruses affecting citrus, lumbard trees. In fact the methods of the present invention have general application to a very large number of plant viral diseases.

Plants treated with the active ingredients of the present invention are of a general nature and include by example only the plants mentioned in the previous paragraph.

Reference is also made to the attached drawings wherein: FIG. 1 shows the inhibition of TMV replication in tobacco leaf discs by 2′,5′-adenylate trimer core, AMP and adenosine. TMV-infected tobacco leaf discs, treatment and TMV determination. TMV content of the discs in the presence of 2′,5′-adenylate trimer core (▲) was compared to TMV content of discs in the presence of AMP (○) and adenosine (●). FIG. 2 shows time course of TMV replication in the presence of 2′,5′-adenylate trimer core of 2′,5′-cordycepin trimer core. Discs were removed at various times after TMV inoculation and their TMV content was determined. Kinetics of TMV replication in the absence (●) ore presence of $2 \times 10^{-7}$ M 2′,5′-adenylate trimer core (■) or $2 \times 10^{-7}$ M 2′,5′-cordycepin trimer core (▲) are indicated.

Without further elaboration, the foregoing will so fully illustrate my invention that others may, by applying current or future knowledge, readily adapt the same for use under various conditions of service.

I claim:

1. The method of inhibiting viral diseases in intact, growing plants comprising applying to a part of said plants an effective amount of a dimeric to decameric oligonucleotide of purine aglycones, said oligonucleotide being linked in a 2′,5′-phosphodiester bond, said oligonucleotide being provided in an inert vehicle, said oligonucleotide being applied to said plant part without a coprecipitant, in an amount not less than $10^{-14}$ moles/cm² of plant part.

2. The method of claim 1 wherein said plant part is a leaf.

3. The method of claim 1 wherein said plant part is a root.

4. The method of claim 2 wherein said active agent is selected from the group consisting of 2′,5′-oligonucleotide with 5′ external phosphate moiety.

5. The method of claim 2 wherein said active agent is selected from the group consisting of 2′,5′-oligonucleotide without 5′ external phosphate moiety.

6. The method of claim 2 wherein said active agent is 2′,5′-oligoadenylate.

7. The method of claim 2 wherein said active agent is dephosphorylated 2′,5′-oligoadenylate (core).

8. The method of claim 2 wherein said active agent is dephosphorylated 2′,5′-adenylate dimer (core).

* * * * *